(12) United States Patent
Anderson et al.

(10) Patent No.: US 10,345,140 B1
(45) Date of Patent: Jul. 9, 2019

(54) IMPEDANCE TUBE AND SAMPLE HOLDER

(71) Applicants: Ryan Bruce Anderson, Great Mills, MD (US); Bradley Yost, Lexington Park, MD (US); Matthew Stone, Lexington Park, MD (US); Tiffany Lei, La Plata, MD (US)

(72) Inventors: Ryan Bruce Anderson, Great Mills, MD (US); Bradley Yost, Lexington Park, MD (US); Matthew Stone, Lexington Park, MD (US); Tiffany Lei, La Plata, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/951,384

(22) Filed: Apr. 12, 2018

(51) Int. Cl.
*G01N 29/09* (2006.01)
*G01H 15/00* (2006.01)

(52) U.S. Cl.
CPC .............. *G01H 15/00* (2013.01); *G01N 29/09* (2013.01)

(58) Field of Classification Search
CPC .. G01H 15/00; G01H 15/0806; G01N 11/142; G01N 11/165; G01N 2021/6482; G01N 23/20025; G01N 25/486; G01N 29/09; G01N 29/22; G01N 29/221; G01N 29/222; G01N 29/223; G01N 29/226; G01N 29/24; G01N 29/2462; G01N 29/2475; G01N 2291/018; G01N 2291/0191; G01N 2291/0237

USPC .... 73/589, 23.41, 24.01, 40.5, 61.55, 61.58, 73/61.59, 61.68
See application file for complete search history.

(56) References Cited

U.S. PATENT DOCUMENTS

| | | | | |
|---|---|---|---|---|
| 6,119,521 A | * | 9/2000 | Shivashankara | G01N 29/11 181/284 |
| 6,612,156 B1 | * | 9/2003 | Hakimuddin | B01F 3/1242 73/597 |
| 2004/0035208 A1 | * | 2/2004 | Diaz | G01N 29/024 73/597 |
| 2017/0276540 A1 | * | 9/2017 | Qiu | G01H 15/00 |

* cited by examiner

*Primary Examiner* — Natalie Huls
*Assistant Examiner* — Suman K Nath
(74) *Attorney, Agent, or Firm* — Mark O. Glut; NAWCAD

(57) ABSTRACT

An impedance tube and sample tube holder that includes a hollow tube, a first tube, a second tube, and a spool. The hollow tube has two halves which are detachable and can hold spacers and a sample. The first tube includes a first tube speaker end and a first tube spool end. The first tube has a speaker disposed at the first tube speaker end and microphones. The second tube includes an anechoic terminator tube end and a second tube spool end. The second tube has microphones and an anechoic terminator at the anechoic terminator tube end. The spool holds the hollow tube with the spacers and the sample. The spool is attachable to the first tube spool end and the second tube spool end such that the sample is perpendicularly orientated to an incoming sound wave produced by the speaker.

1 Claim, 4 Drawing Sheets

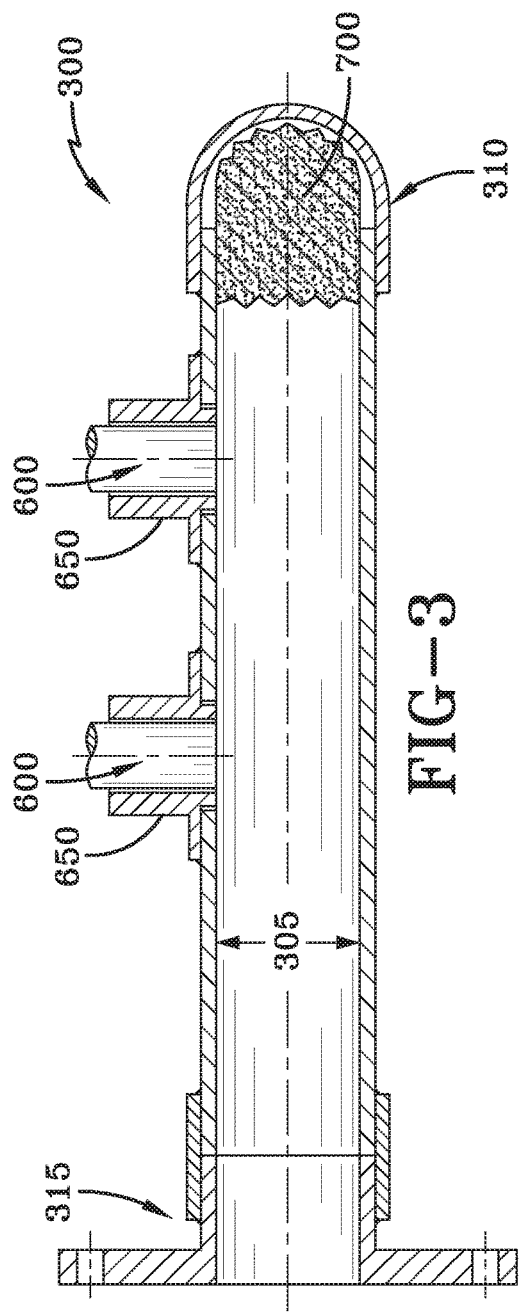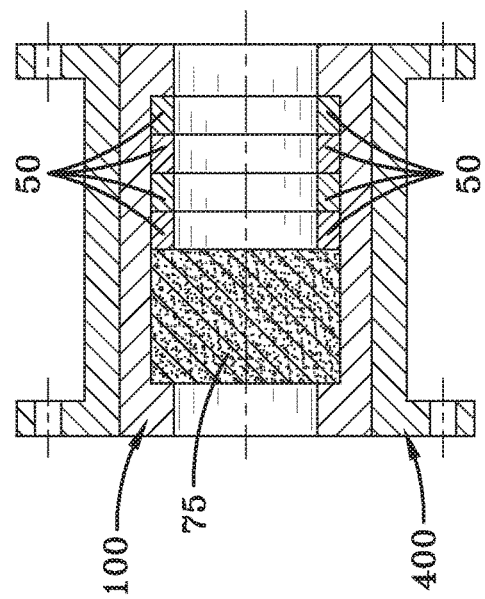

IMPEDANCE TUBE AND SAMPLE HOLDER

STATEMENT OF GOVERNMENT INTEREST

The invention described herein may be manufactured and used by or for the Government of the United States of America for governmental purposes without payment of any royalties thereon or therefor.

BACKGROUND

An impedance tube is a test apparatus that utilizes a speaker to produce a standing wave and microphones to measure the sound characteristics of a sample. Typical sound characteristics measured in an impedance tube are impedance, transmission, and absorption. Currently, a typical impedance tube sample holder is a tube with a constant inner diameter throughout the tube, with the typical sample being foam, or the like. Values can only be reliable if the test sample is oriented perpendicular to the incoming sound wave and if the relative distance of sample to microphones is known. To test acoustical materials, particularly acoustic metamaterials, the sample must be adhered to the tube. Typical impedance tubes require their sample outer diameter be about 0.4% smaller than sample holder diameter. Utilizing rigid samples, the samples are either too large or too small, and not within the required tolerances. Additionally, ASTM standards require certain placement of the sample within the impedance tube. Furthermore, the samples for acoustic metamaterials are prone to rotating within the currently used tube, causing the metamaterial sample to not be oriented perpendicularly to the sound wave. As a result, currently available impedance tubes cannot be utilized to test acoustic metamaterials accurately.

SUMMARY

The present invention is directed to an impedance tube and sample holder that meets the needs listed above and below.

The present invention is directed an impedance tube and sample holder that includes a hollow tube including a lower half tube and a upper half tube such that the lower half tube and the upper half tube are detachable and correspond to form the hollow tube such that the hollow tube can hold spacers and a sample; a first tube with a first tube inner diameter, a first tube speaker end, and a first tube spool end, the first tube having a speaker disposed at the first tube speaker end, and further including measurement microphones that are flush with the first tube inner diameter, a second tube with a second tube inner diameter, an anechoic terminator tube end and a second tube spool end, the second tube having measurement microphones that are flush with the second tube inner diameter, the second tube having an anechoic terminator at the anechoic terminator tube end; and, a spool for holding the hollow tube with the spacers and the sample, the spool disposed within the hollow tube, the spool attachable to the first tube spool end and the second tube spool end such that the sample is perpendicularly orientated to an incoming sound wave produced by the speaker.

It is a feature of the present invention to provide an impedance tube and sample holder that restrains a sample in the longitudinal direction vice the radial direction, the test sample can be oriented perpendicular to the incoming sound wave, and the test sample can be positioned a defined distance from measurement microphones.

It is a feature of the present invention to provide an impedance tube and sample holder that accommodates a wide range of sample thickness, and holds the sample in the correct location at all times.

DRAWINGS

These and other features, aspects and advantages of the present invention will become better understood with reference to the following description and appended claims, and accompanying drawings wherein:

FIG. 3 is a side cross sectional view of an embodiment of the second tube;

FIG. 4 is a side cross sectional view of an embodiment of the spool and the hollow tube;

DESCRIPTION

Figure 1:
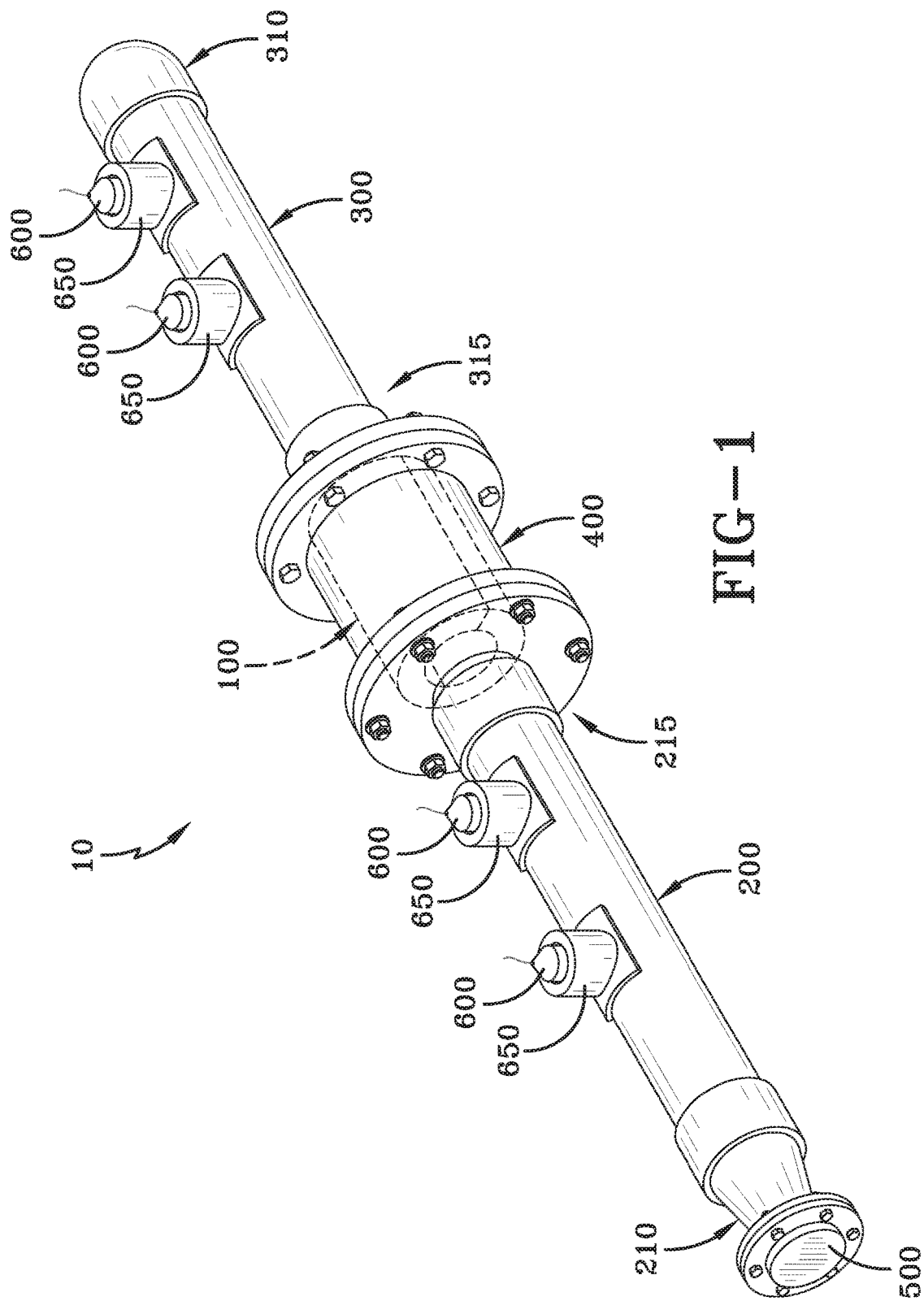
FIG. 1 is a side perspective view of an embodiment of the impedance tube and sample holder.
Figure 2:
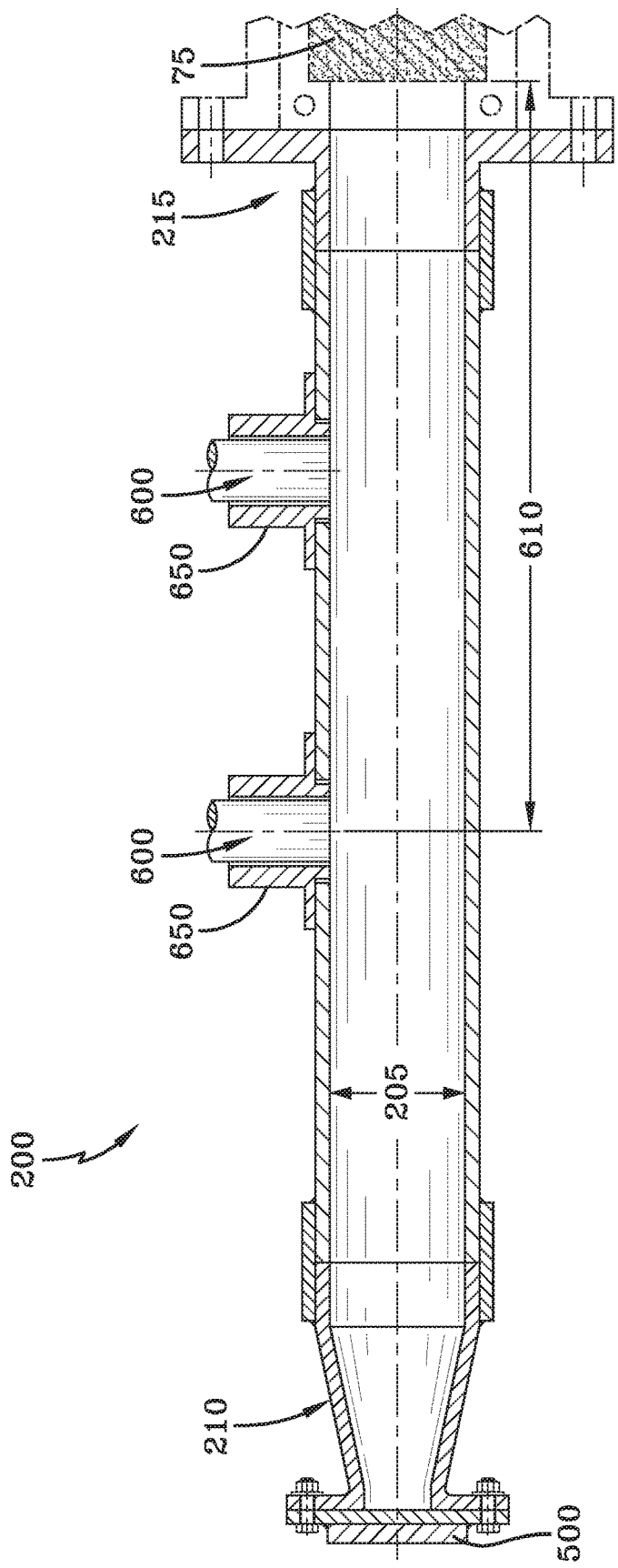
FIG. 2 is a side cross sectional view of an embodiment of the first tube.
Figure 5A:
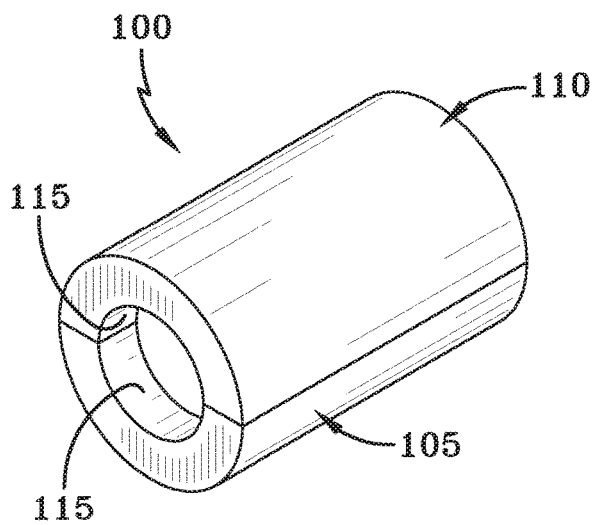
FIG. 5A is a perspective view of an embodiment of the hollow tube.
Figure 5C:
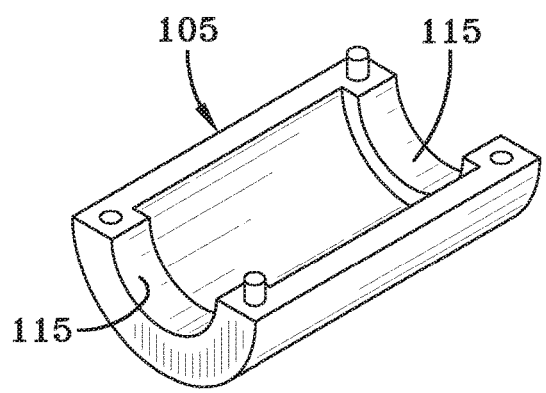
FIG. 5C is a side perspective view of an embodiment of a half of the hollow tube.
Figure 5B:
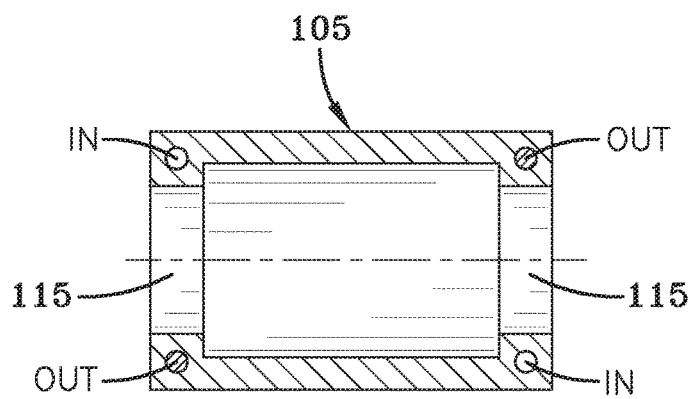
FIG. 5B is a top view of an embodiment of a half of the hollow tube.
Figure 5D:
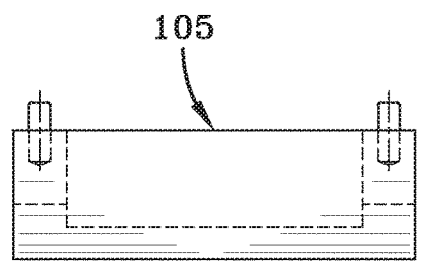
FIG. 5D is side view of an embodiment of a half of the hollow tube.
Figure 5E:
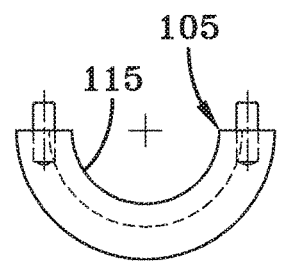
FIG. 5E is a front view of a half of the hollow tube.

The preferred embodiments of the present invention are illustrated by way of example below and as shown in FIGS. 1 through 5E. As shown in FIG. 1, the impedance tube and sample tube holder 10 includes a hollow tube 100, a first tube 200, a second tube 300, and a spool 400. As shown in FIGS. 4 and 5A-5E, the hollow tube 100 includes a lower half tube 105 and a upper half tube 110 such that the lower half tube 105 and the upper half tube 110 are detachable and correspond to form the hollow tube 100 such that the hollow tube 100 can hold spacers 50 (annular) and a sample of acoustic metamaterial 75. As shown in FIG. 2, the first tube 200 includes a first tube inner diameter 205, a first tube speaker end 210, and a first tube spool end 215. The first tube 200 has a speaker 500 disposed at the first tube speaker end 210, and further includes measurement microphones 600 that are flush with the first tube inner diameter 205. As shown in FIG. 3, the second tube 300 includes a second tube inner diameter 305, an anechoic terminator tube end 310 and a second tube spool end 315. The second tube 300 has measurement microphones 600 that are flush with the second tube inner diameter 305, and an anechoic terminator 700 at the anechoic terminator tube end 310. As shown in FIG. 4, the spool 400 is for holding the hollow tube 100 with the spacers 50 and the sample of acoustic metamaterial 75 disposed within the hollow tube 100. The spool 400 is attachable to the first tube spool end 215 and the second tube spool end 315 such that the sample of acoustic metamaterial 75 is perpendicularly orientated to an incoming sound wave produced by the speaker 500.

In the description of the present invention, the invention will be discussed in a military environment to hold and measure acoustic metamaterial samples; however, this invention can be utilized for any type of application that requires use of an impedance tube.

Throughout the impedance tube and sample tube holder 10, the inner cross sectional area is constant. The first tube inner diameter 205 corresponds to the inner diameter of the sample 75, as well as the spacers 50, the second tube inner diameter 305, and a hollow tube diameter 115 (the smallest diameter on the hollow tube and shown in FIG. 5A). The second tube inner diameter 305 corresponds to the inner diameter of the spacers and the sample. The inner diameters of the spacers 50 correspond to the inner diameter of first impedance tube 205 and the second impedance tube 305. The spacers also have an inner diameter that matches the inner diameter of the impedance tube.

In the preferred embodiment, the impedance tube and sample tube holder 10 includes microphone holders 650 for holding and attaching the measurement microphones 600 to their corresponding tubes 200, 300. The microphone holders 650 are positioned to accurately maintain distances between microphones and sample leading surface (the distance between microphone and a sample leading surface is shown in FIG. 2 as 610).

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment(s) contained herein.

What is claimed is:

1. An impedance tube and sample holder comprising:

a hollow tube including a lower half tube and a upper half tube such that the lower half tube and the upper half tube are detachable and correspond to form the hollow tube such that the hollow tube can hold spacers and a sample of acoustic metamaterial where the sample covers the entire cross-sectional area of the hollow tube;

a first tube with a first tube inner diameter, a first tube speaker end which is a closed end of the first tube, and a first tube spool end, the first tube having a speaker disposed at the first tube speaker end, and further including measurement microphones that are placed flush with the first tube inner diameter;

a second tube with a second tube inner diameter, an anechoic terminator tube end and a second tube spool end, the second tube having measurement microphones that are placed flush with the second tube inner diameter, the second tube having an anechoic terminator at the anechoic terminator tube end; and a spool for holding the hollow tube with the spacers and the sample, the spool disposed within the hollow tube, the spool attachable to the first tube spool end and the second tube spool end such that the sample is perpendicularly orientated to an incoming sound wave produced by the speaker, the speaker disposed at a predefined distance from the measurement microphones.

* * * * *